United States Patent [19]

Mittleman

[11] 4,405,316

[45] Sep. 20, 1983

[54] INJECTION SITE WITH CHECK VALVE INLET

[75] Inventor: Herbert Mittleman, Deerfield, Ill.

[73] Assignee: Baxter Travenol Laboratories, Inc., Deerfield, Ill.

[21] Appl. No.: 892,766

[22] Filed: Apr. 3, 1978

[51] Int. Cl.³ .............................................. A61M 5/14
[52] U.S. Cl. ...................................... 604/86; 604/247
[58] Field of Search ............ 128/214 R, 214 C, 214.2, 128/227; 210/DIG. 23, 436; 604/82–86, 247

[56] References Cited

U.S. PATENT DOCUMENTS

| | | | |
|---|---|---|---|
| 3,332,418 | 7/1967 | Brody | 128/214 R |
| 3,886,937 | 6/1975 | Bobo et al. | 128/214 R |
| 4,000,740 | 1/1977 | Mittleman | 128/214 R |
| 4,048,996 | 9/1977 | Schopen et al. | 128/214 R |

Primary Examiner—Dalton L. Truluck
Attorney, Agent, or Firm—Paul C. Flattery; John P. Kirby, Jr.; George H. Gerstman

[57] ABSTRACT

A check valve housing is rigidly attached to the first inlet of an injection site having a body portion, a first inlet, a second inlet and an outlet. The check valve housing encloses a duckbill valve member and has an interior wall which securely and frictionally engages a portion of the external surface of the duckbill valve member.

6 Claims, 3 Drawing Figures

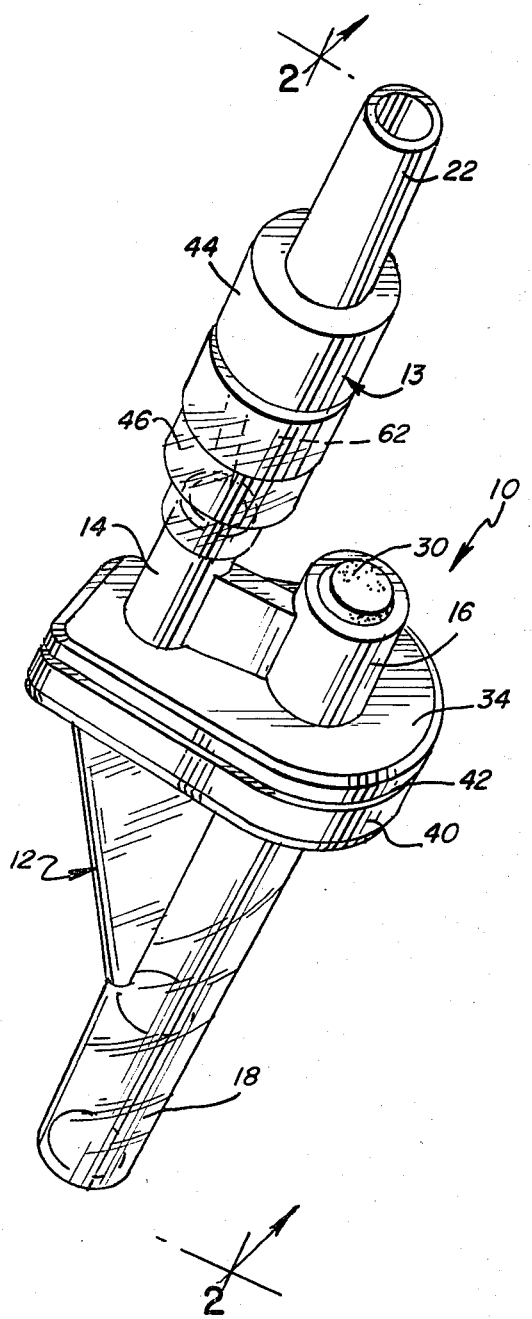
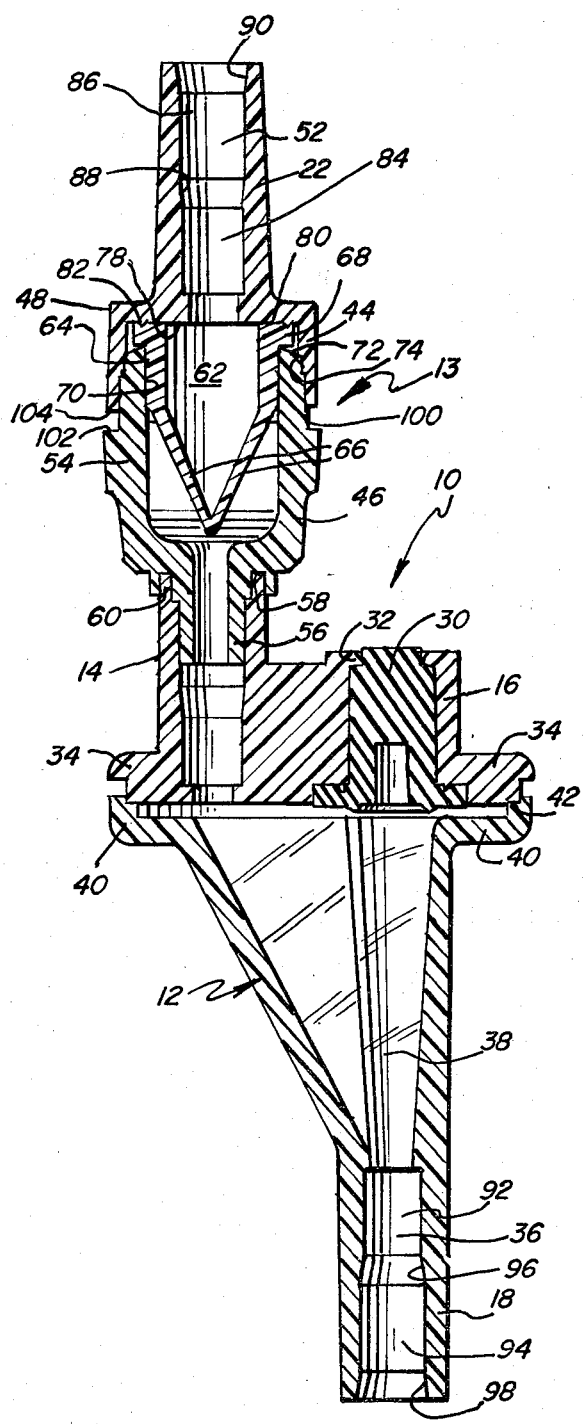
FIG. 1
FIG. 2

INJECTION SITE WITH CHECK VALVE INLET

BACKGROUND OF THE INVENTION

This invention relates to an improved injection site.

Injection sites are commonly used in hospitals where a parenteral fluid is being fed to a patient intravenously and it is also desired to combine another medicament with the parenteral fluid. In such circumstances, the parenteral fluid is fed via flexible conduit to one inlet of a connecting device, commonly called an injection site. Flexible conduit extends from the outlet of the injection site to an appropriate device for administering the liquid to the patient. The injection site typically carries a second inlet, having a pierceable diaphragm connected thereto. The supplementary medicament may be injected into the second inlet by a hypodermic syringe and it becomes combined with the parenteral liquid for administration to the patient.

Injection sites are commonly used with administration sets such as illustrated in British Pat. No. 1,182,016 entitled "Parenteral Administration of Liquids". Thus a container of parenteral liquid is fed via flexible tubing (through a tubing clamp) to a burette having a main chamber and a downstream drip chamber, from the drip chamber and via flexible tubing (through another tubing clamp) to an injection site, through the injection site and via flexible tubing to a hypodermic needle for intravenous connection to the patient. A sequence of events is required to be performed by an operator for priming the drip chamber in this prior art administration set. Thus the tubing clamp between the drip chamber and the injection site is opened, the drip chamber is squeezed, the tubing clamp is closed while the drip chamber is still being squeezed, and the drip chamber is released after the tubing clamp is closed.

I have discovered a novel injection site which, when connected to the drip chamber outlet, obviates the need for a tubing clamp between the drip chamber and the injection site and obviates the need for the above-mentioned sequence of steps to be performed by an operator for priming the drip chamber. When my novel injection site is connected to the outlet of the drip chamber, in order to prime the drip chamber the drip chamber is merely squeezed and released, and a check valve which forms a part of the injection site automatically restricts back flow and allows the drip chamber to be properly primed.

In U.S. Pat. No. 3,886,937, issued June 3, 1975, a tubular "Y" administration set is disclosed for sequentially delivering a plurality of medical liquids to a patient over prolonged periods of time. A low pressure responsive valve is located in a first arm of the "Y" set, having a structure that opens and closes the first arm in response to changes in relative surface level heights of two gravity feed liquids supplied to the administration set's first and second arms. The patent does not disclose the priming of a drip chamber by merely squeezing and releasing the drip chamber. Additionally, the low pressure responsive valve which is illustrated in duckbill form in one embodiment of the patent, grasps the outside of a collar which may result in separation of the duckbill valve from the housing.

Injection sites having a shape which permits laminar flow of the fluid are disclosed in U.S. Pat. Nos. 4,000,740 and 4,048,995, issued Jan. 4, 1977 and Sept. 20, 1977, respectively, and entitled "Injection Site".

The instant invention is an improvement with respect to the injection sites disclosed in these patents.

It is an object of the present invention to provide an injection site having a check valve housing rigidly attached to the first inlet thereof.

Another object of the present invention is to provide an injection site which is simple in construction and easy to manufacture.

A further object of the present invention is to provide an injection site which, when connected to the outlet of a burette drip chamber, obviates the need for a tubing clamp to be interposed between the drip chamber outlet and the injection site.

A still further object of the present invention is to provide an injection site having a check valve housing rigidly attached to the first inlet, with the check valve housing being constructed to hold securely a duckbill valve member therein.

A further object of the present invention is to provide an injection site to which flexible tubing of different diameters may be connected.

Other objects and advantages of the invention will become apparent as the description proceeds.

BRIEF DESCRIPTION OF THE INVENTION

In accordance with the present invention, there is provided an injection site having a body portion, a first inlet, a second inlet with a self-sealing, pierceable member located therein and an outlet. The improvement comprises a check valve housing rigidly attached to the first inlet, with the check valve housing enclosing a check valve member acting to permit fluid flow in only one direction. The check valve housing has an interior wall which securely and frictionally engages a portion of the external surface of the check valve member.

In the illustrative embodiment, the check valve member comprises a duckbill valve. The housing comprises a lower member and an upper member. The lower and upper members are connected and are cooperative to provide indicium of a proper and secure connection between the upper and lower members.

In the illustrative embodiment, the check valve housing has an interior top wall which abuts the top of the check valve member. The interior top wall includes a downwardly extending annular rib for engaging securely the top of the check valve member. The lower member has an angled portion which cooperates with the upper member to become forced against the exterior of the check valve member when the lower and upper members are assembled, to aid in preventing the check valve member from separating from the housing.

A more detailed explanation of the invention is provided in the following description and claims, and is illustrated in the accompanying drawings.

BRIEF DESCRIPTION OF THE DRAWINGS

FIG. 1 is a perspective view of an injection site constructed in accordance with the principles of the present invention;

FIG. 2 is a cross-sectional elevation thereof, taken along the plane of the line 2—2 of FIG. 1.

DETAILED DESCRIPTION OF THE ILLUSTRATIVE EMBODIMENT

Figure 3:
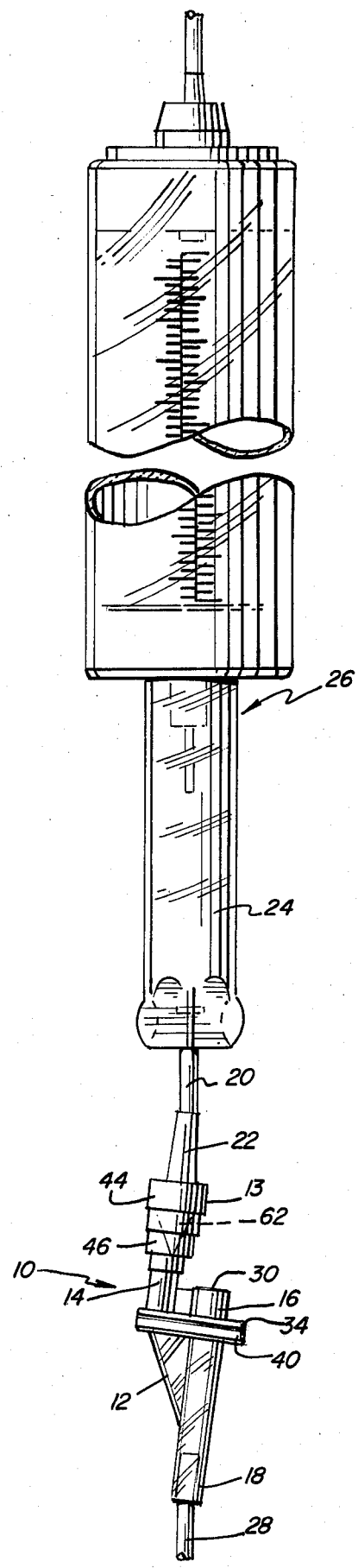
FIG. 3 is a front elevational view of the injection site of FIG. 1 connected to the drip chamber of a burette from an administration set.

Referring to the Figures, there is shown an injection site 10 having a main body portion 12, a check valve housing 13, a first inlet 14, a second inlet 16 and an outlet 18. As illustrated in FIG. 3, flexible plastic conduit 20 has its downstream end coupled to a rigid inlet 22 of the check valve housing 13, and the upstream end of conduit 20 is connected to an outlet of drip chamber 24 of burette 26. The upstream end of flexible conduit 28 is connected to outlet 18 of injection site 10.

A pierceable, resealable diaphragm 30, which may be formed of Latex rubber, extends into second inlet 16 and is held under compression by annular flange 32 (FIG. 2).

Inlets 14 and 16 are formed of a non-pierceable plastic material and are molded in a unitary assembly including first inlet 14, second inlet 16 and circumferential flange 34. Body portion 12 is also formed of a non-pierceable plastic material and includes outlet 18, the walls of which define a bore 36 communicating with a main chamber 38 of the body portion. Inlets 14 and 16 and outlet 18 all communicate with main chamber 38 with the second inlet 16 being coaxial with outlet 18.

Body portion 12 is also molded as a unitary assembly including outlet 18, the walls defining chamber 38 and flange 40. Flanges 34 and 40 are sonically welded together at 42 to complete the assembly.

Although no limitation is intended, example dimensions which may be used in forming corresponding portions of the injection site are set forth in U.S. Pat. No. 4,048,995.

Check valve housing 13 comprises an upper member 44 and a lower member 46. Upper member 44 is integrally formed with a circumferential rim 48 and a rigid inlet 22, with the walls of inlet 22 defining an axial bore 52. Lower wall 46 is integrally formed with a circumferential sidewall portion 54 and a slotted lower extension 56. Lower extension 56 defines an annular slot 58 which cooperates with upper rim 60 of inlet 14 whereby the upper rim is inserted into the slot 58 and this effect double seal is sonic-welded.

The check valve 62 located within check valve housing 13 preferably comprises a duckbill valve member, having a generally cylindrical upper portion 64 and a pair of duckbill lips 66 which angle inwardly and downwardly to meet and form a normally closed valve. With respect to FIG. 2, fluid flow in a downward direction will open lips 66 while fluid flow in an upward direction will be prevented by the check valve 62.

A sealing rim 68 is formed at the top of cylindrical body portion 64 of the check valve, and extends outwardly to provide more effective sealing between the check valve and the check valve housing 13. As shown most clearly in FIG. 2, the external surface of check valve 62 is securely and frictionally engaged by the interior wall 70 of lower housing portion 46. Further, the top 72 of lower housing portion 46 is angled inwardly and upwardly and cooperates with an inverted shoulder 74 of upper housing member 44 to form a wedge which pinches check valve 62, thereby enhancing the security of the check valve.

It can also be seen from FIG. 2 that upper housing member 44 has an interior top wall 78 which abuts the top 80 of check valve 62. Further, wall 78 carries a downwardly extending annular rib 82 which cooperates with wedging angle 72 to squeeze flange 68 of check valve 62, thereby further securing the check valve in place within housing 13.

Check valve 62 is preferably formed of silicone, which is compatible with both blood and parenteral solutions. The check valve housing 13 is preferably formed of plexiglas DR, which has been found effective for both molding and sterilization purposes.

The walls of rigid inlet 22 defining bore 52 allow for connection of different size tubing to inlet 22. To this end, a relatively small diameter bore 84 is formed at the downstream end of inlet 22 and a larger diameter bore portion 86 is formed at the upstream end thereof. An outward taper 88 is provided between bore portions 84 and 85 and an outward tapered portion 90 is provided upstream of bore portion 86. Tapered portions 88 and 90 act as reservoirs and wipers for excess solvent. Thus when the flexible tubing, such as flexible PVC tubing, is connected to inlet 22, the tubing is immersed in methylethylketone solvent and then inserted into bore 52. If there is too much solvent on the flexible tubing, tapered portion 88 or 90 acts to squeeze the flexible tube and collect the solvent at the top.

Likewise, the interior wall of outlet 18 defining bore 36 defines a relatively smaller diamter bore portion 92 and a relatively larger diameter bore portion 94, with the smaller diameter bore portion 92 being upstream of the larger diameter bore portion 94. Outwardly and downwardly tapered portions 96 and 98 are provided in a manner analogous to tapered portions 88 and 90 as described above.

Upper housing member 44 is sonically welded to lower housing member 46. Because of the sonic-welding, it may be difficult to determine if the duckbill valve 62 is seated properly within the housing. To this end, a gauge slot 100 is provided to determine if the parts are properly fitted. Thus lower housing member 46 carries a shoulder 102 which is spaced from the bottom 104 of upper housing member 44 a predetermined distance when the parts are fitted correctly. By noting the distance between shoulder 102 and bottom 104, the proper seating of the check valve 62 within the housing 13 can be determined.

It is preferred that body member 12 be of unitary construction and formed of a transparent plastic material so that the nurse or other operator can view the injection site to determine whether air bubbles are present. Injection site 10 can be sold as a portion of an administration kit, if desired. To this end, as illustrated in FIG. 3, a portion of the kit could comprise a burette 26 having a drip chamber 24, the outlet of which is coupled via flexible tubing 20 to rigid inlet 22. By virtue of the check valve located in the manner described above, there is no need to position a tubing clamp between the drip chamber 24 and the injection site. In order to prime drip chamber 24, the operator merely needs to press the drip chamber and then release it, and the check valve will prevent back flow. It is to be understood, however, that the injection site of the present invention could be used in other environments.

It can be seen that an injection site has been shown and described which is simple in construction and economical to manufacture. The check valve carried by the injection site is securely maintained within the check valve housing and in combination with an administration set, the priming of the burette drip chamber is simplified.

Although an illustrative embodiment of the invention has been shown and described, it is to be understood that various modifications and substitutions may be made by those skilled in the art without departing from the novel spirit and scope of the present invention.

What is claimed is:

1. In an injection site having a body portion, a first inlet, a second inlet with a self-sealing, pierceable member located therein and an outlet, the improvement comprising, in combination:

a check valve housing rigidly attached to said first inlet, said check valve housing enclosing a check valve member which acts to permit fluid flow in only one direction; and said housing having an interior wall which securely and frictionally engages a portion of the external surface of the check valve member, said housing comprising a lower member; means attaching the lower member to said first inlet; and an upper member;

means connecting said upper member to said lower member, said upper member and said lower member cooperating to provide indicium of a proper and secure connection between said upper and lower members.

2. A device as described in claim 1, said indicium comprising a measurable gauge slot defined by said upper and lower members.

3. A device as described in claim 1, said lower member having an angled portion which cooperates with said upper member to become forced against the exterior of said check valve member when said lower and upper members are assembled, to aid in preventing the check valve member from separating from the housing.

4. In an injection site having a body portion, a first inlet, a second inlet with a self-sealing, pierceable member located therein and an outlet, the improvement comprising, in combination:

a check valve housing rigidly attached to said first inlet, said check valve housing enclosing a check valve member which acts to permit fluid flow in only one direction; and said housing having an interior wall which securely and frictionally engages a portion of the external surface of the check valve member, including means rigidly attaching said check valve housing to said first inlet, said attaching means comprising an annularly slotted bottom housing portion with a complementary annular rim, carried by said first inlet, being located within said annular slot; said bottom housing portion and rim being fused together.

5. In an injection site having a body portion, a first inlet, a second inlet with a self-sealing, pierceable member located therein and an outlet, the improvement comprising, in combination:

a check valve housing rigidly attached to said first inlet, said check valve housing enclosing a duckbill valve member which acts to permit fluid flow in only one direction;

said housing having an interior wall which securely and frictionally engages a portion of the external surface of the duckbill valve member;

said housing comprising a lower member, means attaching the lower member to said first inlet, and an upper member;

means connecting said upper member to said lower member, said upper member and said lower member cooperating to provide indicium of a proper and secure connection between said upper and lower members, said indicium comprising a measurable gauge slot defined by said upper and lower members;

said housing having an interior top wall which abuts the top of said duckbill valve member, said interior top wall including a downwardly extending annular rib for engaging securely the top of said duckbill valve member;

and said lower member having an angled portion which cooperates with said upper member to become forced against the exterior of said duckbill valve member when said lower and upper members are assembled, to aid in preventing the duckbill valve member from separating from the housing.

6. A device as described in claim 5, including means rigidly attaching said check valve housing to said first inlet, said attaching means comprising an annularly slotted bottom housing portion with a complementary annular rim, carried by said first inlet, being located within said annular slot; said bottom housing portion and said rim being fused together.

* * * * *